United States Patent [19]
Grossi et al.

[11] Patent Number: 5,669,906
[45] Date of Patent: Sep. 23, 1997

[54] GROOVED ROLLER ELECTRODE FOR A RESECTOSCOPE

[75] Inventors: Benedetto Grossi, Stamford, Conn.; Robert Quint, Jamaica, N.Y.

[73] Assignee: Circon Corporation, Santa Barbara, Calif.

[21] Appl. No.: 316,494

[22] Filed: Sep. 30, 1994

[51] Int. Cl.$^6$ .................................... A61B 17/36
[52] U.S. Cl. ...................... 606/46; 606/41; 606/45; 606/49
[58] Field of Search ................ 606/32, 34, 41, 606/45–50

[56] References Cited

U.S. PATENT DOCUMENTS

| | | |
|---|---|---|
| 642,849 | 2/1900 | Otto . |
| 4,095,601 | 6/1978 | AuFranc . |
| 4,314,559 | 2/1982 | Allen . |
| 4,532,924 | 8/1985 | Auth et al. . |
| 4,765,331 | 8/1988 | Petruzzi et al. . |
| 4,917,082 | 4/1990 | Grossi et al. . |
| 5,007,907 | 4/1991 | Nishigaki et al. ............. 606/46 |
| 5,088,998 | 2/1992 | Sakashita et al. ............. 606/46 |
| 5,395,363 | 3/1995 | Billings et al. . |

OTHER PUBLICATIONS

The Use of the Resectoscope in Gynecology, Richard A. Auhll, pp. 91–99, Biomedical Business International, Oct. 11, 1990.

Transurethral Vaporization of the Prostate (T.V.P.): New Horizons Irving M Bush, M.D., Edward Malters, MD Jan Bush R.N. poster presentation, SMIT, Nov., 1993, Orlando, Florida.

*Primary Examiner*—David M. Shay
*Attorney, Agent, or Firm*—Daniel J. Meaney, Jr.

[57] ABSTRACT

A grooved roller forming part of an electrode for use with a resectoscope is shown. The electrode includes an electrode lead member having an elongated conductor member. The elongated conductor member has a first end and a second end with an insulative cover extended therebetween. The first end has a protruding electrode adapted to be electrically connected to an electrosurgical generator and the second end terminates in an active member. An electrode support member is operatively connected to the active member. The electrode support member has an elongated semi-rigid bifurcated arm terminating in a conductive core spaced a predetermined distance from the active member. The bifurcated arm is covered with an insulative material except at the distal end where the grooved roller is located. The electrode support member has a grooved roller having a central opening extending therethrough for rotatably mounting the grooved roller on the conductive core of the support member.

A method for treating and vaporizing tissue, such as prostate tissue, using the grooved roller electrode for a resectoscope is also shown.

19 Claims, 1 Drawing Sheet

GROOVED ROLLER ELECTRODE FOR A RESECTOSCOPE

BACKGROUND OF THE INVENTION

1. Field of the Invention

The invention relates generally to an electrode having a rotatable element adapted for use with an endoscope for tissue ablation and more particularly relates to an electrode having a grooved roller for use in performing procedures, such as, for example, in the genitourinary tract on soft tissue, including bladder and prostrate, for hemostasis, incision, excision and ablation or in performing gynecological procedures such as endometrial ablation.

2. Description of the Prior Art

Use of resectoscopes to treat tissue in the genitourinary tract is well known. Typical of such resectoscopes are the devices disclosed in U.S. Pat. Nos. 5,151,101 and 4,955,884.

Resectoscopes used for transurethral resection of the prostrate (TURP) have four elements, a resectoscope sheath, sometimes referred to as a sheath or an outer sheath, a working element, an electrode and a telescope. The electrodes are operatively connected to a working element and a telescope is slideably inserted through the working element and into position along side of the electrode. Certain electrodes include an electrode stabilizer which is adapted to receive the telescope. The so assembled working element, telescope and electrode are removeably inserted into the sheath to perform a procedure.

In a typical urological procedure, the outer sheath, having an obturator and telescope inserted therein, is visually passed through the urethra to the vicinity of the prostrate and/or bladder neck. The electrode, which is also known as a resectoscope electrode, is typically in the form of a cutting loop located at the distal end of an electrode lead member.

An electrosurgical current, which may be either a coagulation current, a cutting current or some blend thereof is applied to the cutting loop. The energized cutting loop is moved across and cuts the tissue being treated. The cutting loop can also be used to coagulate the wound. In urological procedures, the peak voltage of the electrosurgical cutting currents are typically in the range of 225 volts to about 250 volts at a power level of between about 120 watts to about 200 watts.

A resectoscope electrode having a stabilized cutting loop for a resectoscope is described in U.S. Pat. No. 4,917,082.

The resectoscope electrode described in U.S. Pat. No. 4,917,082 is adapted for use with a urological endoscope or resectoscope. The electrode comprises an electrode lead, an electrode end and an electrode stabilizer. U.S. Pat. No. 4,917,082 discloses that the electrode may take the form of a coagulating electrode, knife electrode, retrograde knife electrode, punctate electrode or roller electrode having a smooth exterior surface.

Continuous flow resectoscopes which utilize a cutting loop electrode for urological procedures are well known in the art and an example of a continuous flow resectoscope is disclosed in U.S. Pat. No. 3,835,842.

An article entitled "THE USE OF THE RESECTOSCOPE IN GYNECOLOGY" by Richard A. Auhll which appeared at pages 91 through 99 of the Oct. 11, 1990 issue of Biomedical Business International (the "Auhll Reference") disclosed the use of a uterine resectoscope system in the form of a continuous flow resectoscope using an electrosurgical electrode for performing intrauterine procedures.

The Auhll Reference discussed three electrode structures, namely: (1) an electrosurgical cutting loop to treat fibroid tissues; (2) a roller ball having a smooth exterior surface for endometrial ablation (which is cauterization of the endometrium); and (3) electrosurgical needle to cut through and destroy tissue producing intrauterine synechia. In gynecological procedures, the voltage of the electrosurgical cutting currents are typically in the range of 225 volts to about 250 volts at a power level of between 60 watts and 100 watts.

In order to increase the efficiency of treatment of the prostrate tissue generally, and the treatment of benign hypertrophy of the prostrate (BPH) in particular, several new procedures and devices have been developed. These procedures and devices include the use of a Nd:YAG laser for the coagulation and vaporization of prostate tissue generally referred to as abdominal tissue. In order to use Nd:YAG lasers for treatment of BPH, optical fibers capable of deflecting a Nd:YAG laser energy beam about 70° to about 90° to the axis of the optical fiber (generally known as side-firing fibers) have been developed.

Use of a direct contact laser fiber is discussed in an article entitled "TRANSURETHRAL EVAPORIZATION OF PROSTATE (TUEP) WITH ND:YAG LASER USING A CONTACT FREE BEAM TECHNIQUE: RESULTS IN 61 PATIENTS WITH BENIGN PROSTATIC HYPERPLASIA" by Perinchery Narayan, M.D., George Fournier, M.D., R. Indudhara, M.D., R. Leidich, M.D., K. Shinohara, M.D. and Alex Ingermann, M.D. which appeared at pages 813 through 820, in the June, 1994, Volume 43, Number 6, Issue of Urology (the "Narayan et al. Reference"). The Narayan et al. Reference discusses the use of laser surgery for BPH as a promising alternative to traditional TURP. The Narayan et al Reference discloses that in prostate surgery tissue evaporization referred to as Transurethral Evaporization of Prostate Tissue ("TUEP") was achieved by holding the laser fiber in contact with the area to be treated. The TUEP was performed using an Ultraline Laser Fiber manufactured by Heraeus LaserSonics, Milpitas, Calif. The Ultraline Laser Fiber uses a 600 µm internal reflector fiber covered by a guartz glass cap that reflects the Nd:YAG beam at 80 degrees to the fiber axis. This fiber transmits a high-power density beam (spot size of 700 µm and divergence of 17 degrees, giving a power density at 60 watts to 80 watts of 15,600 to 21,231 $Wcm/^2$) 1 mm from the fiber tip. A 23 French cystoscope (CIRCON ACMI, Stamford, Conn.) equipped with an 8 French laser bridge and a continuous flow system was used for the procedure.

The results as state in the Narayan et al. Reference was as follows:

"... Tissue evaporation was achieved by holding the laser fiber in contact with the area to be treated, and by dragging at a rate of 1 cm/20 seconds of laser energy delivery. At the beginning of each furrow dragging was commenced one bulling was seen indicating tissue evaporation. Dragging the fiber at a rate of 1 cm/20 seconds resulted in a furrow 5 to 7 mm deep with a 3 to 4 mm rim of coagulated tissue immediately next to it."

Another known prior art device for treatment of prostate tissue was presented at a poster session at the Society of Minimal Invasive Therapy ("SMIT") on Nov. 5, 1993. The poster session was entitled "TRANSURETHRAL VAPORIZATION OF THE PROSTATE (T.V.P.): NEW HORIZONS" by Irving M. Bush, M.D., Edward Malters, M.D. and Jan Bush, R.N. (the "Bush et al. Reference") disclosed the use of an improved scored ball loop produced by CIRCON ACMI Division of Circon Corporation, assignee of the present patent application, with a continuous flow resectoscope for providing transurethral desiccation (vaporization) of the prostrate.

The Bush et al Reference states as follows:

"T.U.D (transurethral desiccation of the prostate) was first described in 1874 by Bottini. Since 1966 we have used this visually controlled exact vaporization of the prostate in over 500 men with benign hypertrophy, cancer and bladder neck disease.

In the present method (T.V.P., transurethral vaporization of the prostate) a grooved ball electrode and pure electrosurgical cutting current is used to sculpt out the prostatic bed. T.V.P. has the advantage that it causes little or not bleeding, fluid absorption or electrolyte imbalance. Since the residual desiccated tissue (adequate for pathologic review) is removed at the end of the procedure, there is no slough or delayed bleeding (open vessels are closed without retraction). The patient can leave the hospital, voiding (76%) within the 23 hour observation time in most instances. A new improved scored ball loop (A.C.M.I.) to be used with a continuous flow resectoscope has become available.

T.V.P. is a short procedure without sphincter damage which preserves antegrade ejaculation and has a low (2–3%) subsequent procedure rate. Our experience with the last 100 consecutive patients will be detailed."

For purposes of background in electrosurgical treatment of tissue, there are three basic electrosurgical modes: (a) cutting (dissecting) where tissue is severed by a cutting electrode having a radio frequency ("R.F.") cutting current applied to the cutting electrode and the wounded tissue has a layer of coagulation of about 0.5 mm to about 1 mm beyond the cutting area; (b) fulguration where a ball electrode is positioned above the tissue to be treated and an R.F. arc coagulating current flashes from the ball electrode to the tissue to be treated coagulating the tissue; and (c) desiccation where a smooth ball electrode is held in direct contact with the tissue to be treated and a coagulating current of a selected magnitude is applied to the ball electrode vaporizing the tissue.

The first use of electrosurgical generator for prostatic resection using only an R.F. cutting current was in 1931, and the electrosurgical generator was a McCarthy Surgical Unit Type 504A sold by the Complex Oscillator Corporation (the "McCarthy Surgical Unit"). The McCarthy Surgical Unit was a highly efficient vacuum tube generator producing sustained oscillation of high frequency.

The McCarthy Surgical Unit was capable of being used for numerous procedures including prostatic resection. The McCarthy Surgical Unit manual states the following with respect to prostatic resection:

"With the wide interest shown in the relief of prostatic encroachment by the intravesical route, we offer this apparatus as the only present day means for actuating some of the electrodes used for this purpose. The splendid action of this current in a liquid medium has eliminated the hazard of failure at the current source.

The method advocated by Dr. Joseph F. McCarthy, for whom this apparatus was designed, permits great flexibility and with proper technique, the entire prostatic urethra can be remodeled.

The Stern Resectoscope under the able guidance of Dr. T. M. Davis has been modified for greater durability and effectiveness. Other surgical methods that have required the use of high frequency currents have been spurred to new activity.

Here again the requirements have been fully and adequately met and an excess of power provided that will encourage continued research. Those engaged in this specialty are freed of the limitations imposed by generators hitherto available.

In the practice of urology the McCarthy Unit provides every modality. Every purpose which requires the use of high frequency current is served; fulguration of cysts, papillomata, tumors, etc., coagulation control of bleeding, resection and treatment.

The current supplied by the type 504-A unit although very efficacious in resection, shows no effect on delicate insulating materials, greatly prolonging the useful life of urological instruments and electrodes. The selective foot switch permits hemorrhage control with the same electrode used for resection, without the necessity of changing the controls on the apparatus."

The McCarthy Surgical Unit manual states that the McCarthy Surgical Unit can be used for coagulation as follows:

"The unit generates by one type of current, and the controls merely provide the means for adjusting its intensity. It has been established that the same current that shows such admirable cutting characteristics is also the most effective for coagulation. By virtue of its penetrating quality the time necessary for coagulating tumor masses or malignancies has been greatly reduced. Sections of coagulated areas show a tapering off into unaffected tissue that practically eliminates the possibility of secondary hemorrhage. Tumor masses show a remarkable shrinkage during application, proportional to their fluid content.

The technique used in coagulation with this type of current is the same as used for tissue destruction and for hemorrhage control. The electrode must be placed in contact with the area to be treated before the current is turned on. After treatment the current must be off before the electrode is removed. No attempt should be made to ply the area with sparks. In following this technique there is no possibility of carbonization, and no tissue can adhere to the electrode."

The McCarthy Surgical Unit utilized for coagulation and dissection a smooth ball shaped electrode having a 3/16 inch (4 mm) diameter.

The McCarthy Surgical Unit utilized a control panel having two dials. The first dial was referred to as the Range Selector (R.S.) having three ranges, a low, medium and high, each representing one third of the current output. The second dial was referred as the Current Intensity Control (C.I.C.) and provided smooth linear adjustment over each range. Thus, the Range Selector was a course adjustment and the Current Intensity Control was a fine adjustment. The only current produced by the McCarthy Surgical Unit was a cutting current. The maximum current was in the order of 2,600 milliamperes.

In the McCarthy Surgical Unit, for all operative work, dissection, coagulation, bladder fulguration, prostatic resection and the like, a plate electrode was placed under the patient and connected to an indifferent, terminal which is usually a ground terminal, to ground the patient.

In using the McCarthy Surgical Unit for prostatic resection, bleeding resulting from the removal and vaporization of tissue using high intensity cutting current was controlled by passing the same electrode over the same treated tissue area using a low intensity cutting current for providing coagulation of the treated tissue.

Typically, the resulting coagulation layer of the heated tissue had a thickness in the order of 0.5 mm to about 1 mm which appeared sufficient to stop bleeding.

SUMMARY OF THE INVENTION

A novel, new and unique electrode for a resectoscope for performing laparoscopic procedures is disclosed and taught by the present invention. In the preferred embodiment, the electrode comprises an electrode lead member having an elongated conductor member having a first end and a second end with an insulative cover extended therebetween. The first end of the electrode member has a protruding electrode which is adapted to be electrically connected to an electrosurgical generator. The second end of the electrode member terminated in an active member.

The electrode includes an electrode support member operatively connected to the loading member and includes an elongated semi-rigid bifurcated arm terminating in a conductive core spaced a predetermined distance from the active member. The electrode support member has a grooved roller having a central opening extending therethrough for rotatably mounting the grooved roller on the conductive core.

Also, a method for treating tissue is shown. The method comprises the steps of: (i) inserting a sheath having a visual obturator into a urethra; (ii) removing the visual obturator leaving the outer sheath in the urethra; (iii) inserting into a resectoscope working element a telescope and an electrode wherein the electrode has an electrode lead member which includes an elongated conductor member having a first end and a second end with an insulative cover extended therebetween wherein said first end has a protruding electrode adapted to be electrically connected to an electrosurgical generator and wherein said second end terminates in an active member and having an electrode support having an elongated semi-rigid bifurcated arm terminating in a conductive core spaced a predetermined distance from the active member and wherein the electrode support member has a grooved roller having a central opening extending therethrough for rotatably mounting the grooved roller on the hub; (iv) passing the resectoscope working element having the telescope and electrode mounted thereon into the sheath and visually positioning the grooved roller in the proximity of the tissue to be treated; (v) irrigating through the sheath the tissue to be treated with an irrigation fluid; and (vi) applying an electrosurgical cutting current to said grooved roller at a selected voltage level of between about 200 volts to about 300 volts and moving the grooved roller having an electrosurgical cutting current applied thereto over the tissue to be treated to ablate the tissue.

Each of the known prior art devices and method have certain disadvantages.

In performing TURP procedures, a urological procedure using state-of-the-art cutting loop electrodes, the potential of undesirable side effects on the patient such as retrograde ejaculation, incontinence and the required use of a foley catheter for a relatively long period of time, say in the order of 4 to 5 days or more, are becoming objectionable.

The use of laser fibers for treatment of prostatic tissue appears to have less traumatic effect on the patient. However, the efficiency of the procedure in terms of quantities of tissue removed, the technique for using the laser fibers, energy required in joules for vaporizing tissue and the resulting depth of the coagulated layer of tissue are deemed to be short comings to the potential long term use of laser fibers for laser prostatectomy.

The use of scored roller electrode in a resectoscope for treatment of prostatic tissue using cutting current R.F. signals appeared to show that a scored roller ball electrode would successfully vaporize prostatic tissue. However, the removal rate of tissue, the time required for completion of a procedure and the depth of the layer of coagulated tissue appeared to require significant improvement to increase the efficiency of the procedure relative to a laser fiber used for a similar procedure.

Therefore, the problem with the known prior art devices is that the operable power levels in terms of watts are higher than desired using a standard roller ball or a scored roller ball, the size of the craters of vaporized tissue formed in a unit of time is below the desired time verses vaporization results of tissue treatment, the time required to produce trenches of vaporized tissue is longer than desired and the thickness of remaining coagulated tissue is thinner than desired and requires additional coagulating time to develop a sufficient thick coagulate layer of tissue in the area of the treated vaporized tissue.

The grooved roller electrode of the present invention overcomes several of the problems associated with prior art electrodes and devices. The preferred embodiment of the present invention is in the form of a grooved roller which is cylindrically shaped and which has a plurality of circumferentially extending grooves forming central rails and side walls. However, a spherical shaped electrode having circumferentially extending grooves forming central rails and side walls is also capable of vaporizing tissue.

One advantage of the present invention is that the electrode having the grooved roller can be used with standard urological and gynecological resectoscopes.

Another advantage of the present invention is that the grooved roller may have a variety of geometrical shapes such as, for example, a cylindrical shape, a pinion gear shape, a large groove having helical wound wire or other shapes which provide a grooved outer surface having rails or ridges, something liken to a rib. When an R.F. electrosurgical cutting current is applied to the grooved roller, the unique protruding ridge configuration causes areas of high R.F. current concentration or density which provides highly desirable deep tissue penetration. It is desirable for the electrode configuration to have a large number of high current density areas.

Another advantage of the present invention is that the use of grooves, ridges or rails having areas which maximize R.F. current concentration facilitate reduced power requirement, lower power settings on the electrosurgical generator and improved efficiency.

Another advantage of the present invention is that the protruding ridges or rails may have polished surfaces which minimize tissue sticking or adhesion. Thus, as the grooved roller is moved over tissue during treatment, the absence of tissue adhering to the surface of the protruding ridges or rails is desirable to maintain efficiency of vaporization.

Another advantage of the present invention is that the structure of the grooved roller is atraumatic in the non-energized mode.

Another advantage of the present invention is that the grooved roller may be used in urological procedures, gynecological or other procedures requiring tissue vaporization.

Another advantage of the present invention is that the grooved roller can be used with a resectoscope in performing prostatectomy for treatment of BPH of the prostate.

BRIEF DESCRIPTION OF THE DRAWINGS

These and other advantages of the invention will be readily apparent when considered in light of the detailed description hereinafter of the preferred embodiment and of the drawings which include the following figures.

DESCRIPTION OF THE PREFERRED EMBODIMENT

Figure 1:
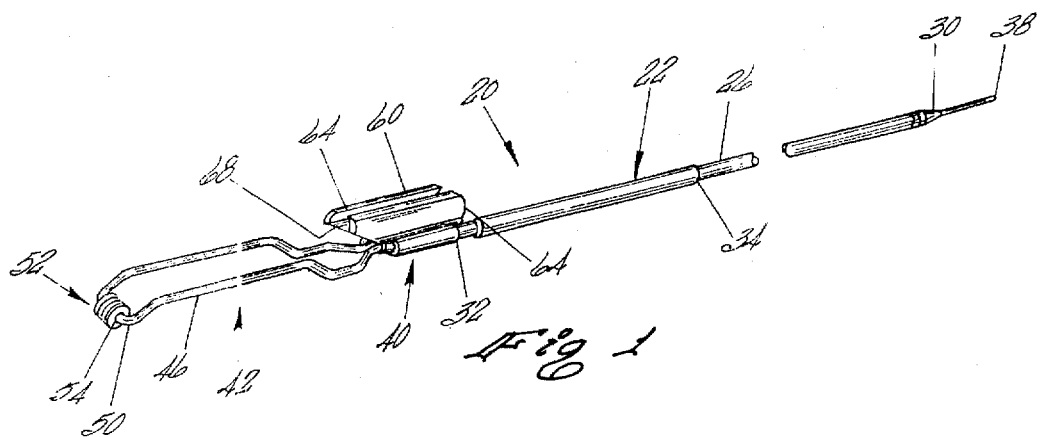
FIG. 1 is a top, front and left side perspective view of a grooved roller electrode for use with a resectoscope.

In the perspective view of the grooved roller electrode of FIG. 1 shown generally as 20. The structure of the electrode is for use with a resectoscope. The electrode 20 includes an electrode lead member 22 having an elongated conductor member 26 having a first end 30 and a second end 32. An insulative cover 34 extends between the first end 30 and the second end 32.

The first end 30 has a protruding electrode 38 which is adapted to be electrically connected to an electrosurgical generator. The second end 32 terminates in an active member or a loading member shown generally as 40.

The active member 40 has an electrode support member, shown generally as 42, operatively connected to the loading member 40. The electrode support member 42 has an elongated semi-rigid bifurcated arm 46 which terminates in a conductive core 50 spaced a predetermined distance from the active member 40. The bifurcated arm 46 has an insulative covering formed thereon except in the portion thereof which forms the conductive core 50.

The electrode support member 42 has a grooved roller 52 having a central opening 54 extending therethrough for rotatably mounting the grooved roller 52 on the conductive core 50.

In the preferred embodiment, the electrode stabilizer 60 for stabilizing the grooved roller 52 is proximate a distal region of a telescope mounted in a resectoscope working element. It is envisioned that the electrode 20 does not need to have the electrode stabilizer 60 in order to practice this invention. The distal end of a telescope is removeably supported by stabilizer 60. The stabilizer 60 has a pair of space resilient support arms 64 which define a hollowed out space 68 to receive a telescope.

The stabilizer 60 is made of a resilient and flexible dielectric material, generally an insulating material, and resiliently literally mount the electrode to a telescope and insulates the electrode 20 from a telescope.

Figure 2:
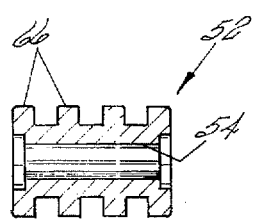
FIG. 2 is a cross-sectional view of a grooved roller shown in FIG. 1 in the form of a cylinder having three spaced circumferentially extending ridges.
Figure 3:
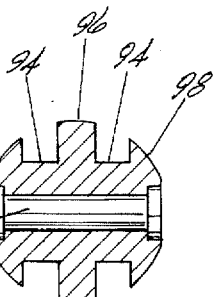
FIG. 3 is a right side elevational view of the grooved roller of FIG. 2.

FIGS. 2 and 3 depict the preferred embodiment of a grooved roller 52 in the form of a cylinder having a plurality of radially extending conductive sections 66. In FIGS. 2 and 3, the plurality of radially extending conductive sections 66 are formed by circumferentially extending slots 68 having a selected depth. The circumferentially extending slots form an outer surface having at least two spaced central ribs 66 and two spaced side rails 70. In the preferred embodiment, the typical depth of the slots 68 would be in the order of 0.012 inches (0.3 mm) and the width of the slots 68 would be in the order of 0.015 inches (0.4 mm). The diameter of the cylinder would be in the order of 0.115 inches to about 0.160 inches (3 to 4.5 mm) and the length would be in the order of 0.115 inches (3 mm).

Since the width of each of the grooves or slots is about 0.4 mm and the selected grooved roller width is about 3 mm, the grooved width is about 13% of the grooved roller width. Thus, in the preferred embodiment the ratio of the grooved width to the grooved roller selected width is selected to be about 0.13. Since the depth of each of the grooves or slots is about 0.3 mm and the grooved roller selected diameter is about 3 mm to about 4.5 mm, the groove depth is about 8.5% to about 12% of the grooved roller selected diameter. Thus, in the preferred embodiment the ratio of the grooved roller depth to the grooved roller diameter is selected to be about 0.1 and in the range of about 0.085 to about 0.12. Since the depth of each of the grooves or slots is about 0.3 mm and the selected groove width is about 0.4 mm, the groove depth is about 75% of the groove width. Thus, in the preferred embodiment the ratio of the groove depth to the groove width is about 0.75.

Figure 4:
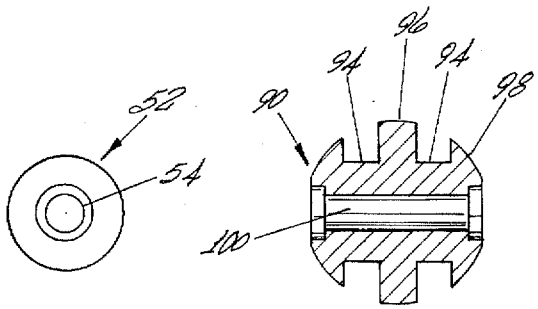
FIG. 4 is a front elevational view of the grooved roller in the form of an ACME thread having helical turns defining raised ridges.

FIG. 4 illustrates another embodiment of a grooved roller 90 which is in the form of a sphere having a pair of circumferentially extending grooves 94 having a selected depth. The grooves 94 form a rail or raised ridge 96 and side rails 98.

The grooved roller 90 has a central opening 100 which is adapted to receive and be rotatable about a conductive core 50 as shown in FIG. 1.

Figure 5:
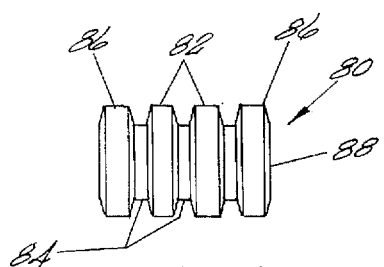
FIG. 5 is a front elevational view of a grooved roller in the form of a sphere having circumferentially extending slots forming raised ridges on the outer surface.

FIG. 5 illustrates another embodiment of a grooved roller 80 which is in the form of an extended cylinder having an ACME thread formed by a helical winding having raised threaded member which define raised ridges 82 and side walls 86 separated by slots 84.

The grooved roller SO has a central opening 86 which is adapted to receive and be rotatable about a conductive core 50 as shown in FIG. 1.

Figure 6:
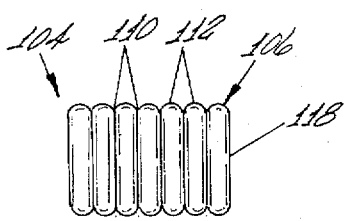
FIG. 6 is a front elevational view of a grooved roller having a serpentine surface.

FIG. 6 illustrates another embodiment of a grooved roller in the form of a cylinder, shown generally as 104, a serpentine surface 106 which defines a plurality of circumferential grooves 110 and raised or protruding ridges 112. A central opening 118 extends axially through the center of the grooved roller 104.

Figure 7:
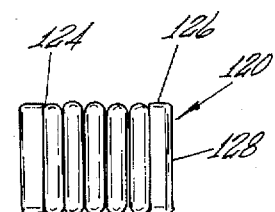
FIG. 7 is a front elevational view of a grooved roller having a single annular shaped circumferential grooves having a helical wire wound in the annular shaped grooved and around the roller.

FIG. 7 illustrates another embodiment of a grooved roller, shown generally as 120, having a single, wide, circumferential elongated groove 124 having side walls 126 formed thereon. A helical wire 120, formed of a conductive material wound around the electrode in the groove 124. In the preferred embodiment, the conductive material may be spring wire.

An elongated opening 128 which extends axially through the grooved roller 120 is adapted to rotatably mount the grooved roller 120 on the conductive core 50 illustrated in FIG. 1.

Figure 8:
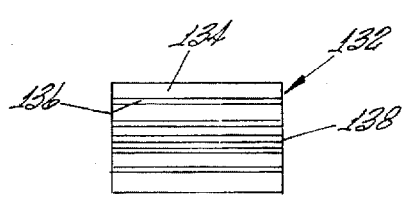
FIG. 8 is a front elevational view of a grooved roller in the form of a pinion gear having a plurality of spaced teeth-like ridges.
Figure 9:
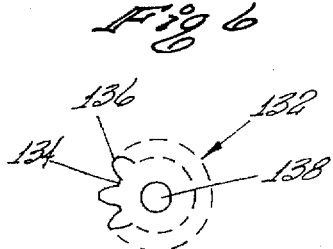
FIG. 9 is a partially diagrammatic view of a right side elevational view of the grooved roller of FIG. 7.

FIGS. 8 and 9 illustrate another embodiment of a grooved roller, shown generally as 132, in the form of an elongated pinion gear having a plurality of raised, radially extending teeth which, by being formed on the surface of the elongated roller, define a plurality of axially extending raised rails or protruding ridges 136. A plurality of axially extending valleys or troughs 138 are located between the axially extending protruding ridges 136. The protruding ridges 136 define areas of high concentration for an R.F. electrosurgical current applied to the grooved roller 132.

The grooved roller 132 has a central opening 138 extending axially therethrough enabling the grooved roller 132 to be rotatably mounted on the conductive core 54 of the bifurcated arm 46 illustrated in FIG. 1.

In use an electrosurgical generator is operatively connected to a resectoscope. The electrosurgical generator produces typical R.F. electrosurgical currents which may be a cutting current, a blend current or a loop current. A description of typical R.F. electrosurgical currents is set forth at pages 96 through 97 and page 100 of the Valleylab SSE4 Instruction Manual.

The electrosurgical current is applied by the grooved roller electrode 20 and the grooved roller 52 to a patient tissue to be treated, A dispersive electrode or patient plate, is affixed to the patient, usually by means of a conductive gel. The dispersive electrode is electrically connected to an isolated terminal. In order to complete the electrical path back to the electrosurgical generator, the electrosurgical generator is electrically connected to the isolated terminal.

Thus, the patient is part of the electrically conductive path. As such, the areas of high concentration of R.F. electrosurgical current which form on the protruding ridges, such as, for example, ridges 66 of the grooved electrode 52, result in areas of increased current density which electrically interact with the tissue being treated. During treatment, the grooved roller 52 is moved gently over the tissue allowing the grooved roller 52 to move without much pressure, not unlike moving a hot knife through butter, vaporizing the tissue forming a trough therein. In this environment, the grooved roller 52 functions as an active electrode while the patient grounding plate functions as a dispersive electrode.

The procedure can be performed with the grooved roller in either air or liquid as a medium. Air provides less electrical resistance such that an electrosurgical voltage of about 200 volts and a power level of between 160 watts to 240 watts will provide the desired cutting action. An electrical surgical voltage of about 300 volts in air produces charring resulting in a tissue layer having high resistance, which is undesirable.

In liquid an electrosurgical voltage of about 300 volts and a power level of between 160 and 240 watts produces the desired cutting action while an electrosurgical voltage of about 400 volts to about 500 volts produces charring of the tissue.

A method for treating tissue can be performed using the grooved roller of the present invention. The method comprises the steps of inserting a sheath, which may be an outer sheath for a continuous flow resectoscope (CFR), having a visual obturator into a urethra.

The next step is removing the visual obturator leaving the outer sheath in the urethra the next provides for inserting into a resectoscope working element a telescope and an electrode wherein the electrode has an electrode lead member includes an elongated conductor member having a first end and a second end with an insulative cover extended therebetween wherein said first end has a protruding electrode adapted to be electrically connected to an electrosurgical generator and wherein said second end terminates in an active member and having an electrode support having an elongated semi-rigid bifurcated arm terminating in a conductive core spaced a predetermined distance from the active member and wherein the electrode support member has a grooved roller having a central opening extending therethrough for rotatably mounting the grooved roller on the conductive core;

the next provides for passing the resectoscope working element having the telescope and electrode mounted thereon into the outer sheath and visually positioning the grooved roller in the proximity of the tissue to be treated.

the next provides for irrigating through the outer sheath the tissue to be treated with an irrigation fluid. However, this step is not required if a non-continuous flow resectoscope is used.

the next provides for applying an electrosurgical cutting current to the grooved roller at a selected voltage level of between about 200 volts to about 300 volts.

the next provides for moving the grooved roller having an electrosurgical cutting current applied thereto over the tissue to be treated to vaporize the tissue.

In the preferred embodiment, the method for treating prostate tissue comprises the step of irrigating through an instrument the prostate tissue to be treated and applying a high electrosurgical cutting current to grooved roller at a selected voltage level of between about 200 volts to about 300 volts, and moving the grooved roller having the electrosurgical cutting current applied thereto over a selected portion of prostate tissue to be treated to vaporize the tissue and form a trough having a coagulation layer of treated tissue of at least 2 mm.

In utilizing the grooved roller electrode 52, the velocity of movement of the grooved roller 52 in prostate tissue is approximately 5 mm/sec. The depth of the trough is in the order of 3 mm.

The R.F. electrosurgical setting cooperates with the raised ridges or protrusion to form areas of increased current densities which generate sufficient current flow at the appropriate voltage levels to vaporize the tissue. The tissue surrounding the vaporized tissue becomes coagulated by the R.F. electrosurgical current at the boundary of the vaporized tissue resulting in a layer of necrosed tissue around the side walls 194 and trough 196. The thickness of the coagulated layer is in the order of about 1.5 mm to about 2 mm. Energy settings in the range of 160 watts to about 250 watts is desired, with the preferred power settings to be about 200 watts.

The preferred embodiment shown and described herein is directed for use in a urological procedure. This is an exemplary use and it is envisioned that the principle and teaching herein could be adapted for other procedures.

As an example, the electrode structure could be designed for use in a gynecological procedure with a gynecological resectoscope for performing endometrial ablation of the uterus or debulking myomas.

Also, various other configurations for the design of the grooved roller are envisioned and the preferred embodiment and species disclosed and described herein are exemplary and are not intended to restrict the inventor to the exemplary configuration disclosed herein.

What is claimed is:

1. An electrode for use with a resectoscope comprising
a conductive grooved roller having a selected width and a central opening extending therethrough for rotatably mounting said grooved roller between a bifurcated arm, said grooved roller having at least two grooves each having a selected width defining at least one protrusion having edges and sidewalls wherein the ratio of each groove width to the grooved roller selected width is selected to be about 0.13 to enable the electrosurgical current to concentrate along said edges of the protrusion for defining areas of increased current densities which generate sufficient current flow to vaaporise tissue and coagulate remaining treated tissue.

2. The electrode of claim 1 wherein said grooved roller has at least two circumferential extending grooves.

3. The electrode of claim 1 wherein said grooved roller has at least two longitudinally extending grooves.

4. The electrode of claim 1 wherein the grooved roller is in the form of a raised threaded member defining a plurality of grooves.

5. The electrode of claim 1 wherein the grooved roller has at least three grooves.

6. The electrode of claim 1 wherein the adjacent grooves define a protrusion having a geometrical shape having at least two exposed sidewalls.

7. The electrode of claim 6 wherein the geometrical shape is substantially rectangular.

8. An electrode for use with a resectoscope comprising
a conductive grooved roller having a selected width adapted to be mounted between a bifurcated arm, said grooved roller having at least two grooves each having a selected width and depth and defining at least one protrusion having edges and sidewalls wherein the ratio of the groove width to the groove depth is selected to be about 0.75 to cause the magnitude of the current densities at the edges of the grooves to be higher than the current densities in the areas between the grooves to enable the electrosurgical current to concentrate along said edges of the protrusion for defining areas of increased current densities which generate sufficient current flow to vaporize tissue.

9. The electrode of claim 8 wherein the grooved roller is in the form of a raised threaded member.

10. An electrode for use with a resectoscope comprising
a conductive grooved roller having a selected width and central opening extending therethrough for rotatably mounting said grooved roller on a conductive core of a bifurcated arm, said grooved roller having at least two grooves each having a selected width defining at least one protrusion having edges and sidewalls wherein the ratio of each groove width to the grooved roller selected width is selected to be about 0.13 to enable the electrosurgical current to concentrate along said edges of the protrusion for defining areas of increased current densities which generate sufficient current flow to vaporize tissue.

11. The electrode of claim 10 wherein said grooved roller has at least two circumferential extending grooves.

12. The electrode of claim 10 wherein said grooved roller has at least two longitudinally extending grooves.

13. The electrode of claim 10 wherein the adjacent grooves define a protrusion having a geometrical shape having at least two exposed sidewalls.

14. The electrode of claim 10 wherein the geometrical shape is substantially rectangular.

15. The electrode of claim 10 wherein the grooved roller has at least three grooves.

16. The electrode of claim 15 where the width of each groove are substantially equal.

17. An electrode comprising
a conductive grooved roller having a selected width and a central opening extending therethrough for rotatably mounting said grooved roller on a conductive core of a bifurcated arm, said grooved roller having at least two grooves each having a selected width defining at least one protrusion having edges and sidewalls wherein the ratio of each groove width to the grooved roller selected width is selected to be about 0.13 to enable the electrosurgical current to concentrate along said edges to form areas of increased current densities which generate sufficient current flow to vaporize tissue and coagulate remaining treated tissue.

18. A method for treating prostate tissue comprising the steps of applying a high electrosurgical cutting current to grooved roller having a selected width and having at least two circumferentially extending grooves each having a selected width defining at least one protrusion having edges and sidewalls wherein the ratio of each groove width to the grooved roller selected width is selected to be about 0.13 to enable the electrosurgical current to concentrate along said edges of the protrusion for defining areas of increased current densities at a selected voltage level of between about 200 volts to about 400 volts; and moving the grooved roller having the electrosurgical cutting current applied thereto over a selected portion of prostate tissue to be treated to vaporize the tissue and form a coagulation layer in a remaining crater of treated tissue of at least 1 mm.

19. A method for treating tissue comprising the steps of inserting an outer sheath having a visual obturator into a urethra;

removing the visual obturator leaving the outer sheath in the urethra;

inserting into a resectoscope working element an electrode wherein the electrode has an electrode lead member includes an elongated conductor member having a first end and a second end with an insulative cover extended therebetween wherein said first end has a protruding electrode adapted to be electrically connected to an electrosurgical generator and wherein said second end terminates in an electrode support having an elongated semi-rigid bifurcated arm terminating in a hub spaced a predetermined distance from the loading member and wherein the electrode support member has grooved roller having a selected width and at least two circumferentially extending grooves each having a selected width defining at least one protrusion having edges and sidewalls wherein the ratio of each groove width to the grooved roller selected width is selected to be about 0.13 to enable the electrosurgical current to concentrate along said edges of the protrusion for defining areas of increased current densities and a central opening extending therethrough for rotatably mounting the grooved roller on the hub;

passing the resectoscope working element having the electrode mounted thereon into the outer sheath and positioning the grooved roller in the proximity of the tissue to be treated;

irrigating through the outer sheath the tissue to be treated with an irrigation fluid; and applying an electrosurgical cutting current to said grooved roller at a selected voltage level of between about 200 volts to about 300 volts; and moving the grooved roller having an electrosurgical cutting current applied thereto over the tissue to be treated to vaporize the tissue.

* * * * *

UNITED STATES PATENT AND TRADEMARK OFFICE
CERTIFICATE OF CORRECTION

PATENT NO. : 5,669,906
DATED : September 23, 1997
INVENTOR(S) : Benedetto GROSSI and Robert QUINT It is certified that error appears in the above-indentified patent and that said Letters Patent is hereby corrected as shown below:

In column 8, line 3, delete "68".
In column 8, line 5, delete "66".
In column 8, line 6, delete "70".

In the claims:

In claim 1, column 11, line 8, change "vaapoise" to --vaporize--.
In claim 8, column 11, line 30, after the word "groove" (first occurrence), replace "width" with --depth--; and after the word "groove" (second occurrence), replace "depth" with --width--.

Signed and Sealed this

Nineteenth Day of May, 1998

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,669,906
DATED : September 23, 1997
INVENTOR(S) : Benedetto Grossi et al It is certified that error appears in the above-identified patent and that said Letters Patent is hereby corrected as shown below:

| | | |
|---|---|---|
| Column 1, | line 11, | "prostrate" should read --prostate--; |
| | line 20, | "prostrate" should read --prostate--; |
| | line 32, | "prostrate" should read --prostate--. |
| Column 2, | line 12, | "prostrate" should read --prostate--; |
| | line 40, | "guartz" should read --quartz--; |
| | line 49, | "results" should read --result--, and "state" should read --stated--. |
| | line 55, | "one" should read --once--. |
| Column 3, | line 4, | "prostrate" should read --prostate--. |
| Column 5, | line 13, | "loading" should read --active--. |
| Column 6, | line 35, | "liken" should read --likened--. |
| Column 7, | line 3, | --longitudinal-- should be inserted before "cross-sectional"; |
| | line 8, | "Fig. 4" should read --Fig. 5--; |
| | line 11, | "Fig. 5" should read --Fig. 4--, and "front elevational" should read --longitudinal cross-sectional--; |
| | line 18, | "grooves" should read --groove--; |
| | line 19, | "grooved" should read --groove--; |
| | line 25, | "Fig. 7" should read --Fig. 8--; |
| | line 59, | "space" should read --spaced--; |
| | line 64, | "literally" should read --laterally--, and "mount" should read --mounts--. |
| Column 8, | line 7, | "68" should be deleted; |
| | line 8, | "68" should be deleted; |
| | line 15, | "grooved" (first occurrence) should read --groove--; |
| | line 16, | "grooved" should read --groove--; |
| | line 44, | "grooved" should read --groove-- and "SO" should read --80--. |
| | line 56, | "120" should read --130--, and --is-- should be inserted after "material". |
| Column 9, | line 3, | "138" should read "--134--; |
| | line 9, | "54" should read --50--; |
| | line 46, | "charting" should read --charring--; |
| | line 60, | --;-- should be inserted before "the next". |

UNITED STATES PATENT AND TRADEMARK OFFICE
CERTIFICATE OF CORRECTION

PATENT NO. : 5,669,906
DATED : September 23, 1997
INVENTOR(S) : Benedetto Grossi et al.

It is certified that error appears in the above-identified patent and that said Letters Patent is hereby corrected as shown below:

| | | |
|---|---|---|
| Column 10, | line 44, | "side" should be deleted; |
| | line 45, | "walls 194 and" should be deleted, and "196" should be deleted. |
| Column 11, | line 11, | "circumferential" should read --circumferentially--; |
| | line 52, | "circumferential" should read --circumferentially--; |

Signed and Sealed this

Fifteenth Day of February, 2000

Q. TODD DICKINSON

*Attest:*

*Attesting Officer*   *Commissioner of Patents and Trademarks*